United States Patent [19]

Ottow et al.

[11] Patent Number: 4,870,069
[45] Date of Patent: Sep. 26, 1989

[54] 11β-ALKYNYL-ESTRENES AND -ESTRADIENES, THEIR PRODUCTION AND PHARMACEUTICAL PREPARATIONS CONTAINING THEM

[75] Inventors: Eckhard Ottow; Rudolf Wiechert; Guenter Neef, all of Berlin; Juergen Bardenhagen, Aachen; Sybille Beier, Berlin; Walter Elger, Berlin; David Henderson, Berlin, all of Fed. Rep. of Germany

[73] Assignee: Schering Aktiengesellschaft, Berlin and Bergkamen, Fed. Rep. of Germany

[21] Appl. No.: 147,475

[22] Filed: Jan. 25, 1988

[30] Foreign Application Priority Data

Jan. 23, 1987 [DE] Fed. Rep. of Germany ....... 3702383

[51] Int. Cl.$^4$ .................. A61K 31/58; A61K 31/56; C07J 1/00
[52] U.S. Cl. ................... 514/179; 260/397.3; 260/397.4; 260/397.45; 514/177; 514/178; 514/182; 514/173; 540/23
[58] Field of Search ............... 260/397.5, 397.3, 397.4, 260/397.45; 514/178, 177, 182, 173, 179; 540/23

[56] References Cited

U.S. PATENT DOCUMENTS 3,236,866  2/1966  Ringold et al. ................. 260/397.3

OTHER PUBLICATIONS

Akzo, CA 107: 127160k (1987).
Shoppee et al., CA 57: 12578 (1962).

Primary Examiner—Douglas W. Robinson
Assistant Examiner—Joseph A. Lipevsky

Attorney, Agent, or Firm—Millen, White & Zelano

[57] ABSTRACT

11β-substituted steroids of the formula

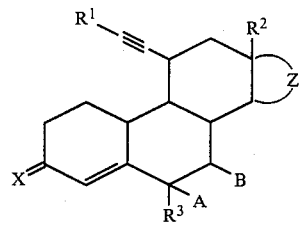

wherein
A and B together represent a second bond between the 6-position and 7-position carbon atoms, or, respectively, are each H;
X is O, two H atoms or hydroximino;
Z is the residue of a pentagonal or hexagonal ring which is optionally substituted and optionally saturated;
$R^1$ is vinyl, $C_{3\text{-}7}$-cyclo-1-alkenyl, phenyl, naphthyl or 5- or 6-membered heterocyclic aromatic having at least one N, O or S atom, each being unsubstituted or substituted by 1-3 halogen atoms, 1-3 $C_{1\text{-}4}$-alkyl, $C_{1\text{-}4}$-alkoxy, $C_{1\text{-}4}$-acyl, $C_{2\text{-}10}$-alkenyl, $C_{1\text{-}4}$-acyloxy, phenyl, nitro, hydroxy, carboxy, cyanide, $COOR^4$ or amino optionally substituted by 1-2 $C_{1\text{-}4}$-alkyl;
$R^2$ is methyl or ethyl,
$R^3$ is H, Cl or methyl; and
$R^4$ is $C_{1\text{-}4}$-alkyl optionally substituted by phenyl which itself is optionally substituted by $C_{1\text{-}4}$-alkyl, $C_{1\text{-}4}$-alkoxy, halogen or phenyl
have valuable pharmacological properties.

20 Claims, No Drawings

11β-ALKYNYL-ESTRENES AND -ESTRADIENES, THEIR PRODUCTION AND PHARMACEUTICAL PREPARATIONS CONTAINING THEM

Background of the Invention

The invention relates to novel 11β-substituted steroids, processes for their production, pharmaceutical preparations containing these compounds, and their use in the production of medicinal agents.

Summary of the Invention

It is an object of this invention to provide new steroid compounds having valuable properties, especially pharmaceutical properties.

Upon further study of the specification and appended claims, further objects and advantages of this invention will become apparent to those skilled in the art.

These objects have been achieved by providing new 11β-substituted steroids of the formula I

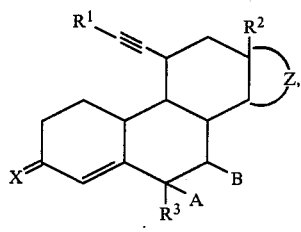

wherein

A and B jointly mean a second bond between the C-6 and C-7 carbon atoms, or, respectively, a hydrogen atom, X is an oxygen atom, two hydrogen atoms or the hydroximino group $N \sim OH$, Z is the residue of a pentagonal or hexagonal ring which is optionally substituted and optionally unsaturated, $R^1$ is a vinyl or cyclo-1-alkenyl residue; a phenyl, naphthyl group or a 5- or 6-membered aromatic with at least one nitrogen, oxygen or sulfur atom; a vinyl or cyclo-1-alkenyl residue, a phenyl, naphthyl group or a 5- or 6-membered aromatic with at least one nitrogen, oxygen or sulfur atom, substituted by 1-3 halogen atoms, 1-3 $C_1$-$C_4$-alkyl groups, a $C_1$-$C_4$-0-alkyl, $C_{1-4}$-acyl, $C_2$-$C_{10}$-alkenyl, $C_1$-$C_4$-0-acyl group, an amino group optionally substituted by one or two $C_1$-$C_4$-alkyl group(s), a phenyl, nitro, hydroxy, carboxy, cyanide or $COOR^4$ residue wherein $R^4$ means a $C_1$-$C_4$-alkyl group optionally substituted by a phenyl group which latter is substituted, if desired, by a $C_1$-$C_4$-alkyl, $C_1$-$c_4$-0-alkyl, halogen, or phenyl residue, $R^2$ is a methyl or ethyl group, $R^3$ is a hydrogen, chlorine atom or a methyl group.

In particular, the invention relates to compounds of general Formula I wherein the fused Z ring is of the formula

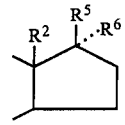

wherein
$R^5/R^6$ mean

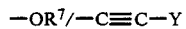

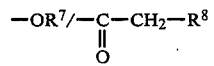

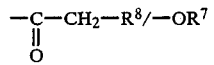

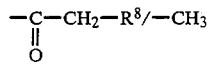

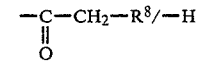

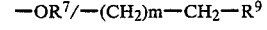

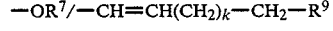

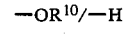

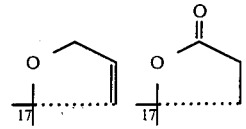

wherein $R^7$ means a hydrogen atom or an acyl residue of 1-4 carbon atoms,

Y means a hydrogen atom, an alkyl, hydroxyalkyl, alkoxyalkyl or acyloxyalkyl group of respectively 1-4 carbon atoms in each of the alkyl and acyl residues, $R^8$ means a hydrogen atom, a hydroxy group, an alkyl, 0-alkyl or 0-acyl group of 1-4 carbon atoms each, $R^9$ means a hydroxy or cyanide residue, an 0-alkyl or 0-acyl group of respectively 1-4 carbon atoms, optionally substituted by 0-alkyl of 1-4 carbon atoms, $R^{10}$ means a hydrogen atom, an alkyl or acyl group of respective 1-10 carbon atoms, m means 0, 1, 2 or 3, k means 0, 1 or 2.

The alkyl, alkoxy as well as acyloxy groups contained in $R^1$, $R^5$ and $R^6$ and, respectively, $R^4$, $R^7$, $R^8$, $R^9$, $R^{10}$ and Y of general Formula I are to have respectively 1-4 carbon atoms, the methyl, ethyl, propyl, isopropyl, methoxy, ethoxy, propoxy, isopropoxy, formyl, acetyl, propionyl and isopropionyl groups being preferred, and the corresponding groups (e.g., alkyl, alkoxy and alkanoyl) based on the n-, i-, s-, and t-butyl isomers also be useful, as well as equivalents of all of these.

Among the alkenyl residues in $R^6$, the propenylene and butenylene groups, which can be present in the E or Z configuration, are preferred; in other words, if $R^6$ stands for $-CH=CH-(CH_2)_k-CH_2-R^9$, then k is to mean preferably zero or 1. Suitable alkenyl residues in $R^1$ are straight- or branched-chain $C_2$-$C_{10}$-, preferably $C_2$-$C_6$-alkenyl groups, such as, for example, vinyl, 1- methylvinyl, propenyl, butenyl or pentenyl. The cyclo-1-alkenyl groups for $R^1$ preferably have 3-7 carbon atoms in the ring. The cyclo-1-pentene and cyclo-1-hexene groups are preferred among the cyclic alkenyl groups. Preferred as the halogen are chlorine and flourine, iodine and bromine also being suitable.

Additional suitable $R^1$ groups are substituted, as well as unsubstituted, phenyl, 1-naphthyl, 2-naphthyl, as well as 5- and 6-membered heterocyclic groups containing at least one nitrogen, oxygen or sulfur atom, e.g., 1-3 such atoms. Examples of suitable heterocyclic groups are 2-furyl, 2-thienyl, 2-pyridyl, 3-pridyl, 4-pyridyl, oxazolyl, thiazolyl, pyrimidinyl, pyridazinyl, pyrazinyl, 3-furyl, 3-thienyl and 2-tetrazolyl.

Monosubstitution is preferred when the aromatic is substituted. Equivalents of the specifically mentioned Z groups are other known D-rings conventional in steroids having related activities. See, for example, U.S. 4,386,085; U.S. 4,536,401; U.S. 4,609,651; U.S. 4,057,561; E.P. 127,864; and E.P. 245,170.

The novel 11β-acetylene-substituted steroids of general Formula I are produced, according to the invention, by means of a coupling reaction performed at about 0°-100° C., preferably at about 20°-80° C., in polar solvents under the action of a suitable coupling reagent (e.g. R.F. Heck, Palladium Reagents in Organic Syntheses, Academic Press 1985, J. Organometal. Chem. 93 : 253 [1975], J. Org. Chem. 31 : 4071 [1966]) on an 11β-ethynyl steroid of general Formula II

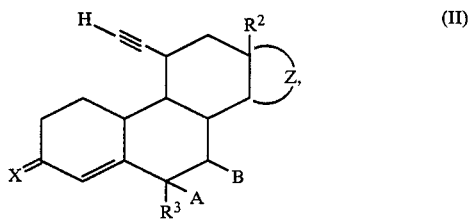

wherein

A, B, $R^2$ nd $R^3$ have the meanings given above, X' is an oxygen atom or two hydrogen atoms, and Z' has the same meaning as Z but any acetylenic hydrogen atoms that may be present in Z are blocked in Z', and also any 0-acyl groups that may be present in Z are present in Z' as OH groups, and any OH groups that may be present in Z or Z' are blocked, if desired, with an aryl, heteroaryl or alkenyl halogenide of general Formula III $$R^{1'} - V \qquad (III),$$

wherein $R^{1'}$ has the same meanings as $R^1$ but any O-acyl groups that may be present in $R^1$ are present in $R^{1'}$ as OH groups, and any OH groups that may be present in $R^1$ or $R^{1'}$ are blocked, if desired, and V is a chlorine, bromine or iodine atom.

Suitable coupling reagents that can be cited are salts and/or complexes of the metals copper, nickel or palladium, or their combinations, used in equimolar to catalytic amounts. In particular, the following are applicable: copper iodide, bis(triphenylphosphine) nickel(II) chloride, tris(triphenylphosphine) nickel, palladium (II) acetate, bis(triphenylphosphine) palladium (II) chloride, bis(triphenylphosphine) acetate, and tetrakis (triphenylphosphine) palladium.

Suitable solvents are, for example, dimethylformamide, hexamethylphosphoric triamide, dimethyl sulfoxide, secondary and tertiary amines, such as diethylamine, dipropylamine, triethylamine, as well as mixtures thereof.

The terminal acetylene blocking groups (for example, the trimethylsilyl or tert-butyldimethylsilyl group) encompassed by Z' in general Formula II are known to one skilled in the art and are cleaved according to methods known from the literature (Synthesis 1980 :627, J. Org. Chem. 46 : 2280 [1986]). The hydroxy blocking groups covered in general Formula II and III by Z' and $R^{1'}$ are groups that can be readily split off in an acidic medium, such as, for example, the methoxymethyl, ethoxymethyl, methoxyethoxymethyl or tetrahdropyranyl group.

The liberated hydroxy groups can be conventionally esterified or etherified.

The thus obtained compounds of general Formula I wherein X means an oxygen atom can be converted, if desired, by reaction with hydroxylamine hydrochloride in the presence of tertiary amines at temperatures of between −20° and +40° C., into the oximes (Formula I wherein X means the hydroximino grouping N~OH and the hydroxy group can be syn or anti positioned). Suitable tertiaryamines are, for example, trimethylamine, triethylamine, pyridine, N,N-dimethylaminopyridine, 1,5-diazabicyclo[4.3.0]nonene-5 (DBN) and 1,5-diaza-bicyclo [5.4.0]undecene-5 (DBU) where pyridine is preferred.

The starting compounds of general Formula II are prepared by formation of the desired structure of the B ring, introduction of the 11β-ethynyl substituent analogously to the direction in German Laid-Open Application DOS 2,805,490 and, respectively, in U.S. Pat. No. 4,292,251 and variation of the D ring and/or of the C-17 substituent pattern according to methods known from the literature; in this connection, the sequence of the aforementioned steps can be altered.

Introduction of the 6,7-double bond is accomplished by allyl or dienol ether bromination and subsequent splitting off of hydrogen bromide.

The allyl bromination is conducted, for example, with N-bromosuccinimide, N-bromoacetamide, 1,3-dibromo-5, 5-dimethylhydantoin or dibromotetrachloroethane in the presence of a radical-forming compound, such as dibenzoyl peroxide, in a solvent. Suitable solvents are aprotic solvents, such as dioxane and chlorinated hydrocarbons, such as, for example, carbon tetrachloride, chloroform or tetrachloroethylene. The reaction takes place between 0° C. and the boiling temperature of the solution.

The dienol ether bromination is carried out, for example, analogously to the direction found in Steroids, I, 233 (se also Fried, Edwards, "Organic Reactions in Steroid Chemistry").

Splitting off hydrogen bromide with formation of the Δ6-double bond takes place by heating the 6-bromo compound with alkaline media, preferably with lithium bromide and lithium carbonate, or with lithium bromide and calcium carbonate, in an aprotic solvlent, e.g. dimethylformamide, at temperatures of 50°-120° C. Another possibility of splitting off HBr resides in heating the 6-bromo compound in collidine or lutidine.

Introduction of the chlorine and, respectively, methyl substituents into C-6 of the steroid skeleton is accomplished, for example, by the methods indicated in German Published Application 1,158,966 and/or in U.S. Pat. No. 4,544,555 and U.S. Pat. No. 4,196,203 by way of the corresponding 6,7-epoxides and, respectively, 6-methylene derivatives.

Removal of the 3-oxo group to obtain a final product of general Formula I wherein X is two hydrogen atoms can be done, for example according to the direction indicated in DOS 2,805,490 by thioketalizing and subsequent reductive cleavage.

Educts having a D-homo steroid structure are produced, for example, by Tiffeneau rearrangement analogously to the direction published in Australian J. Chem. 8 : 519 (1955) and in "Organic Reactions in Steroid Chemistry"2 : 388. The required 17α-aminomethyl-17β-hydroxy compounds are accessible, for example, by way of opening the 17,20-spireopoxides with ammonia or also by lithium aluminium reduction of the acetylated 17β-hydroxy-17α-cyano compounds. The spiroepoxides are obtainable by reacting the corresponding 17-ketones with dimethylsulfonium methylide in dimethylformamide (Journal f. prakt. Chemie 314 :667-668 [1972]). The actylated cyanohydrins can be produced by chemical addition of hydrogen cyanide to the corresponding 17-ketones and subsequent acetylation according to conventional directions (e.g. Australian J. Chem. 8 : 519 [1955]).

Educts with an unsaturated D ring are accessible, for example, by modified Saegusa oxidation (Tetrahedron 42 : 2971 [19896]) of the corresponding enol compounds of the 17-ketone. For example, the trimethylsilyl enol ether can be produced by converting the 17-ketone with lithium diisopropylamide in tetrahydrofuran into the corresponding enolate and scavenging by trimethylchlorosilane (Synthesis 1983 : 1).

The substituents $R^5$ and $R^6$ are introduced according to the usual methods of C-17 side chain construction by nucleophilic addition to the 17-ketone — obtained, for example, by Oppenauer oxidation of the C-17 hydroxy group — and secondary reactions ("Terpenoids and Steroids", Specialist Periodical Report, The Chemical Society, London, vol. 1-12).

Nucleophilic addition of HC≡CY wherein Y is a blocking group, such as, for example, trimethylsilyl or tert-butyldimethylsilyl or alkyl of 1-4 carbon atoms takes place with the aid of a compound of the general formula MC≡CY wherein Y has the meanings given above and M represents an alkali metal.

The organometallic compound can also be formed in situ and made to react with the 17-ketone. Thus, the 17-ketone can be treated, for example, in a suitable solvent with acetylene and an alkali metal, particularly potassium, sodium or lithium, in the presence of an alcohol or in the presence of ammonia. The alkali metal can also be effective in the form of, for example, methyl- or butyllithium. Especially suitable solvents are dialkyl ethers, tetrahydrofuran, dioxane, benzene and toluene.

The introduction of 3-hydroxypropyne, -propene and/or -propane in the 17-position is accomplished by reacting the 17-ketone with the dianion of the propargyl alcohol (3-hydroxypropyne), for example the dipotassium salt of propargyl alcohol, produced in situ, to obtain the 17α-(3-hydroxyprop-1-ynyl)-17β-hydroxy derivative or with metalated derivatives of 3-hydroxypropyne, e.g. with 1-lithium-3-(tetrahydrophyran-2'-ylogy)prop-1-yn-1-ide, to the 17α[3-(tetrahydropyran-2'-ylogy)prop-1-ynyl]-17β-hydroxy derivative; these derivatives can subsequently be hydrogenatd to the 17-(d-hydroxypropyl- and, respectively, -hydroxypropenyl)-17-hydroxy compounds. This is accomplished, for example, by hydrogenation at room temperature and under normal pressure in solvents, such as methanol, ethanol, propanol, tetrahydrofurna (THF) or ethyl acetate with the addition of noble metal catalysts, such as platinum or palladium.

The homologous hydroxyalkyne, hydroxyalkene and hydroxyalkane groups are introduced correspondingly with homologs of propargyl alcohol.

The compound having the Z-configured double bond in the hydroxypropenyl group is formed by hydrogenation of the acetylenic triple bond with a deactivated noble metal catalyst (J. Fried, J.A. Edwards: Organic Reactions in Steroid Chemistry, Van Nostrand Reinhold Company, 1972, page 134; and H.O. House: Modern Synthetic Reactions, 1972, page 19). Examples for suitable deactivated noble metal catalysts are 10% palladium on barium sulfate in the presence of an amine or 5% palladium on calcium carbonate with the addition of lead (II) acetate. Hydrogenation is interrupted after absorption of one equivalent of hydrogen.

The compound with the E-configured double bond in the hydroxypropenyl group is produced by reaction of the acetylenic triple bond in a manner known per se. Quite a number of methods are described in the literature for the conversion of alkynes into trans-olefins, for example reduction with sodium in liquid ammonia (J. An. Chem. Soc. 63 : 216 [1941]), with sodium amide in liquid ammonia (J. Chem. Soc. 1955, 3558), with lithium in low-molecular amines (J. Am. Chem. Soc. 77 : 3378 [1955]), with boranes (J. Am. Chem. Soc. 93 : 3395 [1971]and 94 : 6560 [1972]), with diisobutyl aluminium hydride and methyllithium (J. Am. Chem. Soc. 89 ; 5085 [1967]), and especially with lithium aluminium hydride/alcoholate (J. Am. Chem. Soc. 89 : 4245 [1967]). Another possibility is reduction of the triple bond with chromium (II) sulfate in the presence of water or dimethylformamide in a weakly acidic medium (J. Am. Chem. Soc. 86 : 4358 [1964]), as well as generally reduction by treatment with transition metal compounds with a change in the oxidation stage.

The introduction of the hydroxyalkenes can also be performed directly by addition of a corresponding metalated hydroxyalkenyl compound, e.g. 1-lithium-3-(tetrahydropyran-2'-ylogy)prop-1(E)-ene (J. Org. Chem. 40 : 2265) or 1-lithium-3-(tetrahydropyran-2'-yloxy)prop-1 (Z)-ene (Synthesis 1981 : 999). Homologs can likewise be introduced in this way.

Introduction of 3-hydroxypropane in the 17-position can likewise be carried out directly by reacting the 17-ketone with metalated derivatives of 3-halopropanols—wherein the hydroxy group in the metalating step is present as the alcoholate (Tetrahedron Letters 1978 : 3013) or as a blocked function (J. Org. Chem. 37 : 1947)—to obtain the 17β-(3-hydroxypropyl)-17β-hydroxy compound and, respectively, the compound is blocked at the terminal hydroxy group. Suitable blocking groups are, for example, the ethoxyethyl, tetrahydropyranyl and methoxymethyl groups.

If final products of Formula I are desired wherein $R^5/R^6$ mean

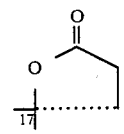

then the 17-(3-hydroxypropyl) compound is conventionally oxidized, for example with Jones reagent, manganese dioxide, pyridinium dichromate, pyridinium chlorochromate, chromic acid-pyridine, or the Fetizon reagent silver carbonate/"Celite" (Compt. rend. 267 : 900 [1968]).

The preparation of final products of Formula I wherein $R^5/R^5$ mean

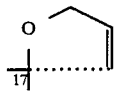

takes place (see also Example 7 below) by ring closure reaction of the corresponding 17α-(3-hydroxyprop-1(Z)-enyl)-17β-hydroxy educt.

Construction of the 17-cyanomethyl side chain is achieved conventionally from the 17-ketone, for example by way of the 17-spiroepoxide and cleavage of the spiroepoxide with HCN according to Z. Chem. 18 : 259-260 (1987).

Also the introduction of the 17-hydroxyacetyl side chain takes place according to methods known per se, for example in accordance with the methods described in J. Org. Chem. 47 : 2993-2995 (1982), Chem. Ber 113 : 1184 (1984), or U.S. Pat. No. 4,600,538.

In orer to introduce the groupings

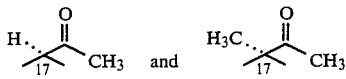

the 17-ketone is converted with tosylmethylisocyanide (Chem. Ind. 1972 : 213 ) into the 17-nitrile compound (Tetrahedron 31 : 2151 [1975]); the last-mentioned compound can be directly converted into the 17-acetyl compound, yielding, after enolizing with potassium tertbutylate in tetrahydrofuran and reaction with methyl iodide, the desired 17α-methyl-17β-acyl grouping. This sequence of adding methyl to the nitrile and subsequent alkylation can also be executed in the reverse order.

Free hydroxy groups in the 17-position and in the residues standing for $R^1$, $R^5$, $R^6$ and Y can be conventionally esterified or etherified.

The novel compounds of general Formula I are valuable pharmaceutical agents suitable for administration to mammals, including humans. Thus, they exhibit strong affinity to the gestagen receptor and display a surprisingly wide range of gestagen, antigestagen, antiglucocorticoid and antimineralocorticoid properties. These important biological efficacies can be exploited for medical purposes.

Because of their antigestagen activity, the compounds are suitable for triggering abortions, since they displace progesterone, required to sustain pregnancy, from the receptor. Therefore, they are valuable and of interest in view of their usage for postcoital fertility control. They can also be utilized against hormonal irregularities, for inducing menstruation, and for initiating labor. Furthermore, they can be used for treatment of hormone-dependent carcinomas. The compounds of general Formula I according to this invention also show antiglucocorticoid activity and consequently can likewise be employed as medicinal agents for the therapy of corticoid-induced disturbances (glaucoma), as well as for combating side effects occurring upon long-term treatment with glucocorticoids (Cushing's syndrome). Therefore, they can also be used for the treatment of disorders resulting from supersecretion of glucocorticoids, above all adiposis, arteriosclerosis, hypertension, osteoporosis, diabetes, as well as insomnia.

Because of their gestagenic activity, the compounds can be utilized, for example, in the therapy of amenorrhea, dysmenorrhea, hypermenorrhea, and luteal insufficiency. Because of their antimineralocorticoid properties, they can be used for treating disease conditions associated with hyperaldosteronism, e.g., as disclosed in U.S. Pat. No. 4,542,128 (column 1, lines 11-13).

As mentioned, all compounds of this invention will have affinity to the gestagen receptor. Whether that affinity results in a gestagenic or antigestagenic effect can be routinely determined in accordance with conventional pharmacological protocols, e.g., as disclosed in U.S. Pat. No. 4,519,946.

Which compounds of this invention have antiglucorticoid activity and/or which compounds have antimineralocorticoid activity can similarly be routinely determined by skilled workers in accordance with conventional pharmacological protocols. For example, U.S. Pat. No. 4,519,946 and G.B. No. 2,118,186 disclose protocols for antiglucocorticoid activity and U.S. Pat.No. 4,536,401 and U.S. Pat. No. 4,540,686 disclose protocols for antimineralocorticoid activity.

The protocol of treating hormone-dependent carcinomas is in Hormonal Manipulation of Cancer: Peptides, Growth factors and New (Anti)-Steroidal Agents, J.G.M. Klijn, R. Paridaens, J.A. Folkers, eds., Raven Press, New York, p. 55 (1987).

Accordingly, the invention likewise relates to medicinal agents based on the pharmaceutically compatible compounds of general Formula I, i.e. compounds that are nontoxic, in the dosages used, optionally together with the customary auxiliary agents and excipients.

The compounds of this invention can be processed according to conventional methods of galenic pharmacy into pharmaceutical preparations for enteral, percutaneous, parenteral, or local administration. They can be administered in the form of tablets, dragees, gelatin capsules, granules, suppositories, implants, injectable sterile, aqueous or oily solutions, suspensions, or emulsions, ointments, creams, or gels.

The active agent or agents can, in this connection, be mixed with the auxiliary materials usual in galenic pharmacy, such as, for example, gum arabic, talc, amylose, mannitol, methylcellulose, lactose, tensides, such as "Tweens" or "Myrj", magnesium stearate, aqueous or nonsqueous vehicles, paraffin derivatives, wetting and dispersing agents, emulsifiers, preservatives, and flavorings to improve taste (for example ethereal oils).

Therefore, the invention also concerns pharmaceutical compositions containing at least one compound of this invention as the active ingredient.

One dosage unit contains about 0.01-1000 mg of active compound(s), preferably 0.04-200 mg.

The preferred dosage ranges for the compounds of this invention when used for the above-described activities are as follows:

(a) Antigestagenic activity: 1-1000 mg/day, preferably 20-200, analogously to the known agent RU 38,486

(b) Antimineralocorticoid activity: 10-1000 mg/day, preferably 50-500, analogously to the known agent spironolactone (c) Antiglucocorticoid activity: 10–10,000 mg/day, preferably 50–1000, analogously to the known agent RU 38, 486

(d) Gestagenic activity: 0.01–5 mg/day, preferably 0.04–0.0, analogously to the known agent gestodene.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees celsius and, unless otherwise indicated, all parts and percentages are by weight.

The entire text of all applications, patents and publications, if any, cited above and below are hereby incorporated by reference.

Examples

The preparation of educts of general Formula II will be described in detail by way of example in connection with seven compounds:

Example 1

17α-(Prop-1-ynyl)-17β-11β-ethynyl-4-estren-3-one (a) At a temperature of 0° C., 17α-(prop-1-ynyl)-11β-ethynyl-3-ethoxy-3, 5-estradien-17β-ol in 1.2 liter of absolute tetrahydrofuran (THF) is saturated with propyne and then 153 ml (245 mmol) of a 1.6-molar n-butyllithium solution (hexane) is gradually added to this solution. After stirring for 30 minutes, a solution of 7.91 g (24.4 mmol) of 11β-ethynyl--3-ethoxy-3,5-estradien-17-one (prepared according to DE 28 05 490 A 1) in 240 ml of absolute THF is added dropwise to this solution. After a reaction time of 2 hours, the reaction mixture is poured on water, and the aqueous phase is extracted with ethyl acetate. The combined organic phases are washed with saturated sodium chloride solution, dried over sodium sulfate, and concentrated using a water jet aspirator, thus obtaining 8.8 g of crude product.

(b) Ten grams of the crude product prepared according to (a) (27.43 mmol) is dissolved in 1 liter of acetone and combined with 50 ml of 4N hydrochloric acid. After one hour of stirring at room temperature, the reaction mixture is combined with 350 ml of saturated sodium bicarbonate solution, and the aqueous phase is extracted repeatedly with methylene chloride. The combined organic phases are dried over sodium sulfate and concentrated using a water jet aspirator. The residue is chromatographed on silica gel with a mixture of hexane/ethyl acetate, thus isolating 7.48 g (81%) 0f 17α-(prop-1-ynyl)-17β-hydroxy-11β-ethynyl-4-estren--3-one; mp 183°–194° C. (crystallized from diisopropyl ether/methylene chloride).

Example 2

17α-(Prop-1-ynyl-17β-hydroxy-11β-ethynyl-4,6-estradien-3-one

A suspension of 8 g of the propynyl compound prepared according to Example 1(a) (crude product = 21.9 mmol) in 100 ml of 80% strength aqueous dioxane is combined with 48 ml of 10% strength sodium acetate solution and cooled to 0° C. In incremental portions, 3.1 g of 1,3-dibromo-5,5-dimethylhydantoin is added to this suspension in such a way that the internal temperature does not rise above +3° C. Subsequently, the mixture is stirred for 30 minutes at 0° C and then the reaction mixture is poured on 100 ml of saturated sodium sulfite solution. The aqueous phase is extracted several times with methylene chloride, the combined organic phases are washed with saturated sodium chloride solution and dried over sodium sulfate. After the solvents have been drawn off, the crude product is taken up in 100 ml of dimethylformamide and combined with 4.75 g of lithium bromide and 3.8 g of lithium carbonate. The reaction mixture is heated for 45 minutes to 100° C. and, after cooling to room temperature, poured on 1.3 liter of water. The aqueous phase is brought to pH 7 with 2N hydrochloric acid and cooled for 30 minutes to 0° C. Thereafter the steroid is removed by filtration, washed with water, and dried under vacuum. This crude product (7.95 g = 96%) has adequate purity for use in the coupling reactions. If the crude produce is further purified by chromatography on silica gel with a mixture of hexane/ethyl acetate, then 5.73 g (78%) of the desired compound is isolated; mp 195–198° C (crystallized from diisopropyl ether).

Example 3

17α-(Prop-1-ynyl)-17β-hydroxy-11β-ethynyl-6-chloro-4,6-estradien-3-one (a) 17α-(Prop-1-ynyl)-17β-hydroxy-11β-ethynyl-6α-7α-epoxy-4-estren-3-one 1.04 g (3 mmol) of 17α-(prop-1-ynyl)-17β-hydroxy-11β-ethynyl-4, 6-estradien-3-one (Example 2) is dissolved in 30 ml of methylene chloride and combined at room temperature with 1.2 g of meta-chloroperbenzoic acid (4.5 mmol) (67.7% strength). The reaction mixture is stirred overnight and then poured on water. After extraction of the aqueous phase with methylene chloride, the combined organic phases are washed in succession with saturated sodium bicarbonate solution, saturated sodium thiosulfate solution, and water, thus isolating 1,099 mg of the desired compound as a crude product.

17α-(Prop-1-ynyl)-17β-hydroxy-11β-ethynyl-6β-chloro-7α-hydroxy-4-estren-3-one

One gram of the compound obtained in (a) is put, at room temperature, into 26 ml of glacial acetic acid and combined with 2 g of lithium chloride. After a further period of stirring for 30 minutes, the reaction mixture is poured on ice water, and the aqueous phase is extracted with methylene chloride. After washing the combined organic phases with water, drying over sodium sulfate, and concentration to dryness, 1.05 g of crude product is isolated. (c) 17α-(Prop-1-ynyl)-17β-hydroxy-11α-ethynyl-6β-chloro-7α-mesyloxy-4-estren-3-one One gram of the crude product obtained in (b) is dissolved in 60 ml of methylene chloride and combined in succession with 3.2 ml (40 mmol) of pyridine and 0.7 ml (9 mmol) of methanesulfonic acid chloride at ice bath temperature. The reaction mixture is gradually brought to room temperature overnight under agitation, then poured on ice water, and the aqueous phase is extracted with methylene chloride. After washing the combined organic phases with saturated sodium bicarbonate solution and drying over sodium sulfate, the phases are concentrated to dryness, thus yielding 1,560 mg of crude product. (d) 17α-(Prop-1-ynyl)-17β-hydroxy-11β-ethynyl-6-chloro-4, 6-estradien-3-one The crude product obtained in (c) is dissolved in 60 ml of absolute dimethylformamide and combined with 3.65 g of sodium acetate. Subsequently, the reaction mixture is heated for 4 hours to 100° C., before being poured on water. The aqueous phase is extracted with ethyl acetate. After washing the combined organic phases with saturated sodium chloride solution and drying over sodium sulfate, the organic solvens are drawn off under vacuum, and the residue is chromatographed on silicia gel with a mixture of hexane/ethyl acetate, thus obtaining 205 mg of the desired product.
N-NMR (CDCl$_3$): δ 6.3 – 6.45 (2H,m,H-4+H--7); 3.0 – 3.5 (1H,mH-11);
1.85 (3H,sCH$_3$—C≡C); 1.22 (3H,s,H-18).

Example 4

17α-Methoxymethyl-17β-hydroxy-11β-ethynyl-4-estren-3-one (a) 11β-Ethynyl-3-ethoxy-3,4-estradiene-[17(η-1') spiro-3']oxirane 1.62 g (5 mmol) of 11β-ethynyl-3-ethoxy-3,4-estradien-17-one is dissolved in 50 ml of absolute dimethylformamide, cooled to 0° C. and combined in succession with 5.1 g (25 mmol) of trimethylsulfonium iodide and 2.9 g (26 mmol) of potassium tert-butylate. The reaction mixture is stirred overnight and gradually warmed to room temperature during this step. Subsequently, the mixture is poured on water and the aqueous phase repeatedly extracted with ethyl acetate. The combined organic phases are washed with saturated sodium chloride solution, dried over sodium sulfate, and concentrated to dryness under vacuum, thus isolating 1.44 g of crude product.

(b) 17α-Methoxymethyl-11β-ethynyl-3-ethoxy-3, 5-estradien-17β-ol 1.35 g (4 mmol) of the crude product obtained in (a) is dissolved in 20 ml of methanol and added to 40 ml of a 3-molar sodium methylate solution (methanolic). The reaction mixture is then heated under reflux until the starting material has been completely reacted. Then the mixture is poured on water, the aqueous phase is extracted with ethyl acetate, and the organic phase is washed with sodium chloride solution. After drying over sodium sulfate and drawing off the solvents under vacuum, 1.45 g of the desired product is obtained as a crude compound.

(c) 17α-Methoxymethyl-17β-hydroxy-11β-ethynyl-4-estren-3-one 1.35 g of the crude product obtained in (b) is dissolved at room temperature in 70 ml of acetone and combined with 3.4 ml of 4N hydrochloric acid (aqueous). After the dienol ether has been completely cleaved (TLC control), the reaction mixture is poured on saturated sodium bicarbonate solution, and the aqueous phase is extracted with methylene chloride. After drying the combined organic phases over sodium sulfate and removal of the solvents under vacuum, the residue is chromatographed on silical gel with a mixture of hexane/ethyl acetate, thus isolating 536 mg of 17α-methoxymethyl-17β-hydroxy-11β-ethynyl-4-estren-3-one.
H-NMR (CDCl$_3$): δ 5.87 (1H,s,H-4); 3.48 and 3.6 (in each
case 1H, d J=10Hz, O-CH$_2$);
3.36 (3H,s,OCH$_3$); 3.0 (1H,m,H-11);
1.23 (3H,s,H-18);
[α]$^{20}$ C $_D$= 92° (CHCl$_3$)

Example 5

17α-(3-Methoxymethoxyprop-1(Z)-enyl)-17β-hydroxy-11β-ethynyl-4-estren-3-one (a) 3-Ethoxy-3,4-estradiene-11,17-dione 49.1 g (172 mmol) of 4-estrene-3,11,17-trione (European Patent Appliction 0 145 493) is dissolved at 0° C. in 180 ml of absolute ethanol and 300 ml of methylene chloride and combined in succession with 51 ml of triethyl orthoformate and 600 mg of p-tolune-sulfonic acid. The reaction mixture is stirred further at the same temperature for 5 hours and then combined with 75 ml of pyridine and 125 ml of water. After stirring for one hour at 0° C., the organic phase is separated and the aqueous phase is extracted with methylene chloride. The combined organic phases are washed with water, dried over sodium sulfate, and concentrated under vacuum. The residue is recrystallized from ethanol, yielding 41 g of the desired enol ether.

(b) 17α-(3-Hydroxyprop-1-ynyl)-17β-hydroxy-3-ethoxy-3, 5-estradien-11-one 30 g of the product prepared (a) is dissolved at 0° C. in 1.2 liter of absolute tetrahydrofuran and combined, under a protective gas, with 220 g of potassium ethylate. To this suspension is added dropwise 77.4 ml of propargyl alcohol and then the reaction mixture is further stirred overnight at 0° C. For working-up purposes, the mixture is poured on water, and the aqueous phase is extracted with methylene chloride. The combined organic phases are washed with saturated sodium chloride solution, dried over sodium sulfate, and concentrated to dryness under vacuum, thus obtaining 38.2 g of crude product.

(c) 17α(3-Hydroxyprop-1(Z)-enyl)-17β-hydroxy--3-ethoxy-3, 5-estradien-11-one

Under normal pressure, 32 g of the crude product obtained in (b) is hydrogenated in a mixture of 325 ml of ethanol and 32.5 ml of pyridine with 3.2 g of palladium/barium sulfate (10% strength). After absorption of one equivalent of hydrogen, the hydrogenation is interrupted by filtration over "Celite"and the filtration is concentrated under vacuum, thus obtaining 32.5 g of a crude product.

(d) 17α-(3-Methoxymethoxyprop-1(Z)-enyl)-17β-hydroxy-3-ethoxy-3, 5-estradien-11-one 30 g of the product obtained in (c) is dissolved in 200 ml of absolute methylene chloride and, at 0° C., combined in succession with 25 ml of diisopropylamine and 9.7 ml of bromomethylmethyl ether. Then the mixture is stirred until complete reaction has occurred (TLC control). The reaction mixture is thereupon poured on water, the aqueous phase is extracted with methylene chloride, and the combined organic phases are washed with saturated sodium chloride solution. After drying over sodium sulfate, the solvents are drawn off under vacuum. The residue is chromatographed on aluminium oxide (neutral, stage III) with a mixture of ethyl acetate/hexane, thus isolating 22.4 g of the desired product.

(e)

17α-(3-Methoxymethoxyprop-1(Z)-enyl-17β-hydroxy-11(E)-methoxymethylene-3-ethoxy-3, 5-estradiene

Under a protective gas, 20 g of the product obtained in (d) is dissolved in 200 ml of absolute toluene and gradually added dropwise at 5° C. to the phosphorylide generated by adding 43 g of potassium tert-butylate to a suspension of 81 g of methoxymethyltriphenylphosphonium chloride in 600 ml of absolute toluene at 0° C under a protective gas. The mixture is agitated until complete reaction has taken place (TLC control). Subsequently the reaction mixture is poured on water, the aqueous phase is extracted with methylene chloride, and the entire organic phase is dried over sodium sulfate. After drawing off the solvents, the residue is chromatographed on aluminium oxide (neutral, state III) with a mixture of hexane/ethyl acetate, yielding 8.4 g of the desired product.

(f)

17α-(3-Methoxymethoxyprop-1(Z)-enyl)-17β-hydroxy-11β-formyl-4-estren-3-one

8 g of the product prepared according to (e) is dissolved in 400 ml of acetone and combined, under a protective gas, with 15 ml of 4N aqueous hydrochloric acid. After stirring for 2 hours at room temperature, the reaction mixture is poured on saturated sodium bicarbonate solution and the aqueous phase is extracted with methylene chloride. The combined organic phases are washed with water and dried over sodium sulfate. After the solvents have been drawn off under vacuum, 6.8 g of a crude product is obtained.

(g)

17α-(3-Methoxymethoxyprop-1(Z)-enyl)-17β-hydroxy-11β-(2-bromo-(Z)-vinyl)-4-estren-3-one

Under a protective gas, 34.2 g of bromomethyl-triphenylphosphonium bromide, suspended in 500 ml of absolute tetrahydrofuran, is combined at −60° C. with 8.8 g of potassium tert-butylate and stirred for 15 minutes. An amount of 6.5 g of the crude product obtained in (f) is dissolved in 75 ml of absolute tetrahydrofuran and slowly added dropwise at −60° C. to the thus-formed ylide. After complete reaction (TLC control), the reaction mixture is poured on water, the aqueous phase is extracted with ethyl acetate, and the entire organic phase is washed with saturated sodium chloride solution. After drying under sodium sulfate, the solvents are drawn off under vacuum. The residue is then chromatographed on silica gel with a mixture of hexane/ethyl acetate, yielding 3.17 g of the desired product.

(h)

17α(3-Methoxymethoxyprop-1(Z)-enyl)-17β-hydroxy-11β-ethynyl-4-estren-3-one

Under a protective gas, 8.8. ml of diisopropyl-amine is combined with 175 ml of absolute tetrahydrofuran, cooled to −10° C., and mixed with 4 ml of 1.6 molar n-butyllithium solution (in hexane). After stirring for 15 minutes at 0° C., the steroid obtained in (g), dissolved in 175 ml of absolute tetrahydrofuran, is added dropwise to this solution at −78° C. After 30 minutes of agitation, the solution is poured on water and the aqueous phase extracted with methylene chloride. The combined organic phases are dried over sodium sulfate and concentrated under vacuum. The residue is chromatographed on silica gel with a mixture of hexane/ethyl acetate, thus obtaining 2.16 g of the desired compound.

H-NMR (CDCl$_3$): δ 5.86 (1H,s broad, H-4); 5.55-5.7 (2H,m,olefin.H); 4.68 (2H,s,O-CH$_2$-O); 4.2 - 4.45 (2H,m,O—CH$_2$-C≡); 3.39 (3H,s,OCH$_3$); 1.27 (3H,s,H-18).

Example 6

17α-(3-Hydroxyprop-1(Z)-enyl)-17β-hydroxy-11β-ethynyl-4-estren-3-one

8 g of the product obtained in Example 5 is dissolved in 50 ml of tetrahydrofuran and combined with 30 ml of 4N hydrochloric acid. The reaction mixture is stirred overnight at room temperature and then poured on saturated sodium chloride solution. The aqueous phase is repeatedly extracted with methylene chloride. The combined organic phases are washed with saturated sodium bicarbonate solution, dried over sodium sulfate, and concentrated under vacuum. The residue is chromatographed on silica gel with a mixture of hexane/ethyl acetate, yielding 5.62 g of the desired product.

H-NMR (CDCl$_3$): δ 5.88 (1H,s broad, H-4); 5.55-5.78 (2H,m,H-olefin.); 4.29 (2H,m,O-CH$_2$—C≡); 1.26 (3H,s,H-18).

Example 7

11β-Ethynyl-4-estrene[17(β-1′)spiro-5′≡]-2′,5′-dihydrofuran-3-one

5.3 g of 17α-(3-hydroxyprop-1(Z)-enyl)-17β-hydroxy-11β-ethynyl-4-estren--3-one (Example 6) is combined with 75 ml of absolute methylene chloride and mixed with 14 ml of triethylamine. The solution is subsequently cooled to 0° C. and combined with 2 ml of methanesulfonic acid chloride by gradual dropwise addition of the latter. After this adding step is finished, the reaction mixture is further stirred for one hour and then poured on saturated sodium bicarbonate solution. The aqueous phase is repeatedly extracted with methylene chloride. The combined organic phases are washed with saturated sodium chloride solution, dried over sodium sulfate, and concentrated under vacuum. The residue is chromatographed on silica gel with a mixture of hexane/ethyl acetate, thus isolating 4.05 g of the desired product.

H-NMR (CDCl$_3$) : δ 5.7-5.95 (3H,m,H-4 + olefin.protons); 4.5-4.62 (2H,m,O—CH$_2$-C≡); 1.26 (3H,s,H-18).

Melting point: 139°-144° C. (ethyl acetate, diisopropyl ether).

General Directions for Palladium-Catalyzed Coupling

Under a protective gas, y mmol of the acetylene component is dissolved in y×45 ml of triethylamine and combined with y×10 mmol of the respective coupling partner. After addition of 10 mol-% of palladium tetrakistriphenylphosphine and 5 mol-% of copper (I) iodide, the mixture is heated to 60° C. until complete reaction has been achieved (TLC control). Subsequently, the reaction mixture is filtered over "Celite" to remove the catalyst, the filtrate is concentrated to dryness, and the residue is chromatographed on silica gel with hexane/ethyl acetate.

| Example | y [mmol] | Yield % | $[\alpha]_D^{20°}$ (c = 0.5; CHCl$_3$) | R$^1$'-V |
|---|---|---|---|---|
| 17α-(Prop-1-ynyl)-17β-hydroxy-11β-[2-(phenyl)ethynyl]estren-3-one | 2 | 82 | +118° | Iodobenzene |
| 17α(Prop-1-ynyl)-17β-hydroxy-11β-[2-(4-dimethylaminophenyl)ethynyl]-4-estren-3-one | 2 | 31 | +146° | 4-Bromo-N,N—dimethylaniline |
| 17α-(Prop-1-ynyl)-17β-hydroxy-11β-[2-(4-methoxyphenyl)ethynyl[-4-estren-3-one | 2 | 75 | +135° | 4-Iodoanisole |
| 17α-(Prop-1-ynyl)-17β-hydroxy-11β-[2-(4-cyanophenyl)ethynyl]-4-estren-3-one | 2 | 76 | +130° | 4-Bromobenzonitrile |
| 17α-(Prop-1-ynyl)-17β-hydroxy-11β-[2-(4-acetylphenyl)ethynyl]-4-estren-3-one | 2 | 90 | +147° | 4-Bromoacetophenone |
| 17α-(Prop-1-ynyl)-17β-hydroxy-11β-[2-(4-acetylphenyl)ethynyl]-4,6-estradien-3-one | 2 | 18 | +300° | 4-Bromoacetophenone |
| 17α-(Prop-1-ynyl)-17β-hydroxy-11β-[2-(4-methoxyphenyl)ethynyl]-4,6-estradien-3-one | 2 | 55 | +239° | 4-Iodoanisole |
| 17α-(Prop-1-ynyl)-17β-hydroxy-11β-[2-(2-thienyl)ethynyl]-4-estren-3-one | 2 | 44 | +145° | 2-Bromothiophene |
| 17α-(Prop-1-ynyl)-17β-hydroxy-11β-[2-(3-thienyl)ethynyl]-4-estren-3-one | 2 | 43 | +127° | 3-Bromothiophene |
| 17α-(Prop-1-ynyl)-17β-hydroxy-11β-[2-(5-formyl-2-thienyl)ethynyl]-4-estren-3-one | 2 | 92 | +155° | 2-Bromo-5-formyl-thiophene |
| 17α-(Prop-1-ynyl)-17β-hydroxy-11β-[2-(3-pyridinyl)ethynyl]-4-estren-3-one | 2 | 81 | +133° | 3-Iodopyridine |
| 17α-(Prop-1-ynyl)-17β-hydroxy-11β-[2-(4-pyridinyl)ethynyl]-4-estren-3-one | 2 | 20 | +124° | 4-Bromopyridine Hydrochloride |
| 17α-(Prop-1-ynyl)-17β-hydroxy-11β-[2-(5-acetyl-2-thienyl)ethynyl]-4-estren-3-one | 2 | 86 | +167° | 2-Bromo-5-acetylthiophene |
| 17α-(Prop-1-ynyl)-17β-hydroxy-11β-(2-phenylethynyl)-4,6-estradien-3-one | 2 | 68 | +235° | Iodobenzene |
| 17α-(Prop-1-ynyl)-17β-hydroxy-11β-[2-(5-isopropoxycarbonyl-2-furyl)ethynyl]-4,6-estradien-3-one | 2 | 66 | +234° | 2-Bromofuran-5-carboxylic Acid Isopropyl Ester |
| 17α-(Prop-1-ynyl)-17β-hydroxy-11β-[2-(3-nitrophenyl)ethynyl]-4-estren-3-one | 2 | 78 | +118° | 3-Bromonitrobenzene |
| 17α-(Prop-1-ynyl)-17β-hydroxy-11β-[2-(2-nitrophenyl)ethynyl]-4-estren-3-one | 2 | 71 | +108° | 2-Bromonitrobenzene |
| 17α-(Prop-1-ynyl)-17β-hydroxy-11β-[2-(2-methoxyphenyl)ethynyl]-4-estren-3-one | 2 | 94 | +145° | 2-Iodoanisole |
| 17α-(Prop-1-ynyl)-17β-hydroxy-11β-[2-(p-tolyl)ethynyl]-4-estren-3-one | 2 | 83 | +128° | 4-Iodotoluene |
| 17α-(Prop-1-ynyl)-17β-hydroxy-11β-[2-(o-tolyl)ethynyl]-4-estren-3-one | 2 | 95 | +131° | 2-Iodotoluene |
| 17α-(Prop-1-ynyl)-17β-hydroxy-11β-[2-(5-isopropoxycarbonyl-2-furyl)ethynyl]-4-estren-3-one | 2 | 65 | +122° | 2-Bromofuran-5-Carboxylic Acid Isopropyl Ester |
| 17α-(Prop-1-ynyl)-17β-hydroxy-11β-[2-(4-fluorophenyl)ethynyl]-4,6-estradien-3-one | 2 | 58 | +204° | 4-Fluoroiodobenzene |
| 17α-(Prop-1-ynyl)-17β-hydroxy-11β-[2-(4-isopropylphenyl)ethynyl]-4,6-estradien-3-one | 2 | 98 | +225° | 4-Iodoisopropylbenzene |
| 11β-[2-(4-Methoxyphenyl)ethynyl]-4-estrene[17 (β-1')-spiro-5']-2',5'-dihydrofuran-3-one | 2 | 54 | +195° | 4-Iodoanisole |
| 11β-[2-Tolylethynyl]-4-estrene[17(β-1')spiro-5']-2',5'-dihydrofuran-3-one | 2 | 73 | +210° | 4-Iodotoluene |
| 17α-(Prop-1-ynyl)-17β-hydroxy- | 2 | 94 | +134° | 2-Bromopropene |

-continued

| Example | y [mmol] | Yield % | $[\alpha]_D^{20°}$ (c = 0.5; CHCl$_3$) | R$^{1'}$-V |
|---|---|---|---|---|
| 11β-(3-methylbut-1-yn-3-enyl)-4,6-estradien-3-one | | | | |
| 17α-(Prop-1-ynyl)-17β-hydroxy-11β-[2-(3-dimethylaminophenyl)ethynyl]-4-estren-3-one | 2 | 34 | +114° | 3-Bromo-N,N—dimethylaniline |
| 17α-(Prop-1-ynyl)-17β-hydroxy-11β-[2-(m-tolyl)ethynyl]-4-estren-3-one | 2 | 90 | +118° | 3-Bromotoluene |
| 17α-(Prop-1-ynyl)-17β-hydroxy-11β-[2-(3,5-dimethylphenyl)-ethynel]-4-estren-3-one | 2 | 83 | +110° | 5-Iodo-m-xylene |
| 17α-(3-Methoxymethoxyprop-1(Z)-enyl)-17β-hydroxy-11β-[2-(2-methoxyphenyl)ethynyl]-4-estren-3-one | 2 | 88 | +140° | 2-Iodoanisole |
| 17α-(3-Hydroxyprop-1(Z)-enyl)-17β-hydroxy-11β-[2-(2-methoxyphenyl)ethynyl]-4-estren-3-one | 2 | 65 | +130° | 2-Iodoanisole |
| 17α-(Prop-1-ynyl)-17β-hydroxy-11β-[2-(3-acetylphenyl)-ethynyl]-4-estren-3-one | 2 | 95 | +121° | 3-Iodoacetophenone |
| 17α-(Prop-1-ynyl)-17β-hydroxy-11β-[2-(1-naphthyl)ethynyl]-4-estren-3-one | 2 | 91 | +148° | 1-Iodonaphthalene |
| 17α-(Prop-1-ynyl)-17β-hydroxy-11β-[2-(3-methoxyphenyl)-ethynyl]-4-estren-3-one | 2 | 93 | +132° | 3-Iodoanisole |

17α-(Prop-1-ynyl)-17β-hydroxy-11β-[2-(phenyl)ethynyl]-4-estren-3-one Antioxime and 17α-(Prop-1-ynyl)-17β-hydroxy-11β-[2-(phenyl)ethynyl)]-4-estren-3-one Synoxime 660 mg (1.6 mmol) of 17-(prop-1-ynyl)-11β-]2-(phenyl)ethyl]-4-estren-3-one is dissolved in 10 ml of pyridine and combined at 0° C. in portions with 560 mg of hydroxylamine hydrochloride. After the addition, the mixture is stirred for 30 minutes at +5° C., poured into a mixture of ice water/0.5N hydrochloric acid, and extracted with dichloromethane. The combined organic phases are concentrated under vacuum. The crude product is chromatographed on silica gel with a mixture of hexane/ethyl acetate, thus isolating 347 mg of 17α-(prop-1-ynyl)-17β-hydroxy-11β-[2(phenyl)ethynyl]-4-estren-3-one antioxime and 155 mg of 17β-(prop-1-ynyl)-17β-hydroxy-11η[2-(phenyl)ethynyl]-4-estren-3-one synoxime.

17α-(Prop-1-ynyl)-17β-hydroxy-11β[2-(phenyl)ethynyl]-4-estren-3-one Antioxime:

H-NMR (CDCl$_3$) : δ 7.3–7.5 (5H,m,aromat.protons); 5.9 (1H,s broad,H-4); 3.3 (1H,mH-11); 1.85 (3H,s,CH$_3$—≡C); 1.25 (3H,s,H-18)

17α(Prop-1-ynyl)-17β-[2-(phenyl)ethynyl]-4-estren-3-one Synoxime:

H-NMR (CDCl$_3$) : δ 7.3–7.5 (5H, aromat.protons); 5.55 (1H,s broad H-4); 3.25 (1H,m,H-11); 1.85 (3H,s,CH$_3$—C≡C); 1.25 (3H,s,H-18)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An 11β-substituted steroid having a 5- or 6-membered D ring wherein rings A-C are of the formula

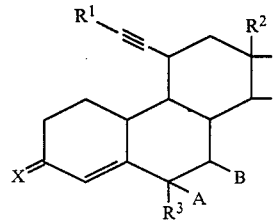

wherein
A and B together represent a second bond between the 6-position and 7-position carbon atoms, or are each H;
X is O, two H atoms or hydroximino;
R$^1$ is vinyl, C$_{3-7}$-cyclo-1-alkenyl, phenyl, naphthyl or a 5- or 6-membered aromatic ring having at least one N, O or S ring atom, each being unsubstituted or substituted by 1-3 halogen atoms, 1-3 C$_{1-4}$-alkyl groups, C$_{1-4}$-acyl, C$_{1-4}$-alkoxy, C$_{2-10}$-alkenyl, C$_{1-4}$-alkanoyloxy, phenyl, nitro, hydroxy, carboxy, cyano, COOR$^4$ or amino optionally substituted by 1-2 C$_{1-4}$-alkyl groups;
R$^2$ is methyl or ethyl,
R$^3$ is H, C1 or methyl; and
R$^4$ is C$_{1-4}$-alkyl optionally substituted by phenyl which itself is optionally substituted by C$_{1-4}$-alkyl, C-hd 1-4-alkoxy, halogen or phenyl.

2. A steroid according to claim 1, wherein the D ring is of the formula wherein
R⁵/R⁶ is

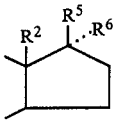

—OR⁷/—C≡C—Y

—OR⁷/—C—CH₂—R⁸
         ‖
         O

—C—CH₂—R⁸/—OR⁷
 ‖
 O

—C—CH₂—R⁸/—CH₃
 ‖
 O

—C—CH₂—R⁸/—H
 ‖
 O

—OR⁷/—(CH₂)$_m$—CH₂—R⁹
—OR⁷/—CH=CH(CH₂)$_k$—CH₂—R⁹, or
—OR¹⁰/—H, respectively, or R⁵ and R⁶ together are

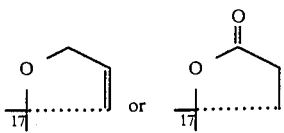

wherein
R⁷ is H or C$_{1-4}$-acyl;
Y is H, alkyl, hydroxyalkyl, alkoxyalkyl or alkanoyloxyalkyl group wherein all alkyl portions have 1-4 carbon atoms;
R⁸ is H, OH, C$_{1-4}$-alkyl, C$_{1-4}$-alkoxy or C$_{1-4}$-alkanoyloxy;
R⁹ is OH, CN, C$_{1-10}$-alkoxy or C$_{1-4}$-alkanoyloxy, optionally substituted by C$_{1-10}$-alkoxy;
R¹⁰ is H, C$_{1-10}$-alkyl or C$_{1-10}$-alkanoyl;
m is 0, 1, 2 or 3; and
k is 0, 1 or 2.

3. A steroid according to claim 1, wherein R³, A and B are each H.

4. A steroid according to claim 2, wherein R³, A and B are each H.

5. A steroid according to claim 1, wherein A and B together are a second bond and R³ is H.

6. A steroid according to claim 2, wherein A and B together are a second bond and R³ is H.

7. A steroid according to claim 1, wherein A and B together are a second bond and R³ is Cl.

8. A steroid according to claim 2, wherein A and B together are a second bond and R³ is Cl.

9. A steroid according to claim 1, wherein A and B together are a second bond and R³ is methyl.

10. A steroid according to claim 2, wherein A and B together are a second bond and R³ is methyl.

11. A steroid according to claim 2, wherein k is 0 or 1.

12. A steroid according to claim 1, wherein the alkenyl substituent of R¹ is branched or straight chained C$_{2-6}$-alkenyl.

13. A steroid according to claim 1, wherein the halogen substituent of R¹ is Cl or F.

14. A steroid according to claim 1, wherein R¹ is cyclo-1-pentene or cyclo-1-hexene.

15. A steroid according to claim 1, wherein R¹ is substituted or unsubstituted phenyl, 1-naphthyl, 2-naphthyl, 2- or 3-furyl, 2- or 3-thienyl, 2-, 3- or 4-pyridyl, oxazolyl, thiazolyl, pyrimidinyl, pyridazinyl, pyrazinyl or 2-tetrazolyl.

16. A steroid according to claim 1, wherein said steroid is
17α-(Prop-1-ynyl)-17β-hydroxy-11β-[2-(phenyl)ethynyl]estren-3-one,
17α-(Prop-1-ynyl)-17β-hydroxy-11β-[2-(4-dimethylamino-phenyl)ethynyl]-4-estren-3-one,
17α-(Prop-1-ynyl)-17β-hydroxy-11β-[2-(4-methoxyphenyl)-ethynyl]-4-estren-3-one,
17α-(Prop-1-ynyl)-17β-hydroxy-11β-[2-(4-cyanophenyl)ethynyl]-4-estren-3-one,
17α-(Prop-1-ynyl)-17β-hydroxy-11β-[2-(4-acetylphenyl)-ethynyl)]-4-estren-3-one,
17α-(Prop-1-ynyl)-17β-hydroxy-11β-[2-(4-acetylphenyl)-ethynyl]-4,6-estradien-3-one,
17α-(Prop-1-ynyl)-17β-hydroxy-11β-[2-(4-methoxyphenyl)-ethynyl]-4,6-estradien-3-one
17α-(Prop-1-ynyl)-17β-hydroxy-11β[2-(2-thienyl)ethynyl]-4-estren-3-one,
17α-(Prop-1-ynyl)-17β-hydroxy-11β[2-(3-thienyl)ethynyl]-4-estren-3-one,
17α-(Prop-1-ynyl)-17β-hydroxy-11β[2-(5-formyl-2-thienyl)-ethynyl)]-4-estren-3-one
17α-(Prop-1-ynyl)-17β-hydroxy-11β[2-(3-pryridinyl)ethynyl[-4-estren-3-one,
17α-(Prop-1-ynyl)-17β-hydroxy-11β[2-(4-pryridinyl)ethynyl]-4-estren-3-one
17α-(Prop-1-ynyl)-17β-hydroxy-11β[2-(5-acetyl-2-thienyl)-ethynyl]-4-estren-3-one,
17α-(Prop-1-ynyl)-17β-hydroxy-11β(2-phenylethynyl)-4,6-estradien-3-one, 17α-(Prop-1-ynyl)-17β-hydroxy-11β-[2-(5-isopropoxycarbonyl-2-furyl)ethynyl]-4,6-estradien-3-one,
17α-(Prop-1-ynyl)-17β-hydroxy-11β[2-(3-nitrophenyl)ethynyl]-4-estren-3-one,
17α-(Prop-1-ynyl)-17β-hydroxy-11β[2-(2-nitrophenyl)ethynyl]-4-estren-3-one,
17α-(Prop-1-ynyl)-17β-hydroxy-11β[2-(2-methoxyphenyl)-ethynyl]-4-estren-3-one,
17α-(Prop-1-ynyl)-17β-hydroxy-11β[2-(p-tolyl)ethynyl]-4-estren-3-one,
17α-(Prop-1-ynyl)-17β-hydroxy-11β[2-(o-tolyl)ethynyl]-4-estren-3-one,
17α-(Prop-1-ynyl)-17β-hydroxy-11β[2-(5-isopropoxycarbonyl-2-furyl)ethynyl]-4-estren-3-one,
17α-(Prop-1-ynyl)-17β-hydroxy-11β[2-(4-fluorophenyl)-ethynyl]-4,6-estradien,3-one,
17α-(Prop-1-ynyl)-17β-hydroxy-11β[2-(4-isopropylphenyl)-ethynyl]-4,6-estradien-3-one,
17α-[2-(4-Methoxyphenyl)-ethynyl]-4-estrene[17(β-1')-spiro-5']-2',5'-dihydrofuran-3-one,
11β-[2-Tolyl)ethynyl]-4-estrene[17 (β-1')spiro-5']-2',5'-dihydrofuran-3-one,
17α-(Prop-1-ynyl)-17β-hydroxy-11β-(3-methylbut-1-yn-3-enyl)-4,6-estradien-3-one,
17α-(Prop-1-ynyl)-17β-hydroxy-11β-[2-(3-dimethylamino-phenyl)ethynyl]-4-estren-3-one, 17α-(Prop-1-ynyl)-17β-hydroxy-11β-[2-(m-tolyl)ethynyl]-4-estren-3-one,
17α-(Prop-1-ynyl)-17β-hydroxy-11β[2-(3,5-dimethylphenyl)-ethynyl]-4-estren-3-one,
17α-(3-Methoxymethoxyprop-1(Z)-enyl)-17β-hydroxy-11β-[2-(2-methoxyphenyl)ethynyl]-4-estren-3-one,
17α-(3-Hydroxyprop-1(Z)-enyl)-17β-hydroxy-11β-[2-(3-methoxyphenyl)ethynyl]-4-estren-3-one,
17α-(Prop-1-ynyl)-17β-hydroxy-11β-[2-(3-acetylphenyl)-ethynyl]-4-estren-3-one,
17α-(Prop-1-ynyl)-17β-hydroxy-11β-[2-(1-naphthyl)ethynyl]-4-estren-3-one, or
17α-(Prop-1-ynyl)-17β-hydroxy-11β-[2-(3-methoxyphenyl)-ethynyl]-4-estren-3-one.

17. A pharmaceutical compositon comprising a compound of claim 1 and a pharmaceutically acceptable carrier.

18. A method of post-coital birth control in a female patient comprising administering an effective amnount of a compound of claim 1 to a patient in need thereof.

19. A method for achieving an antiglucocorticoidal effect in a patient, comprising administering an effective amount of a coumpound of claim 1 to a patient in need thereof.

20. A method for achieving an antimineralocorticoidal effect in a patient, comprising administering an effective amount of claim 1 to a patient in need thereof.

* * * * *